United States Patent
Abolaban et al.

(10) Patent No.: US 10,867,716 B1
(45) Date of Patent: Dec. 15, 2020

(54) SYSTEMS AND METHODS FOR PRODUCING ACTINIUM-225

(71) Applicant: King Abdulaziz University, Jeddah (SA)

(72) Inventors: Fouad Abolaban, Jeddah (SA); Essam M. Banoqitah, Jeddah (SA); Eslam M. Taha, Jeddah (SA); Abdulsalam M. Alhawsawi, Jeddah (SA); Fathi Djouider, Jeddah (SA); Andrew Nisbet, Jeddah (SA)

(73) Assignee: King Abdulaziz University, Jeddah (SA)

( * ) Notice: Subject to any disclaimer, the term of this patent is extended or adjusted under 35 U.S.C. 154(b) by 0 days.

(21) Appl. No.: 17/018,193

(22) Filed: Sep. 11, 2020

(51) Int. Cl.
  *G21G 1/06* (2006.01)
  *A61N 5/10* (2006.01)
  *G21G 1/00* (2006.01)

(52) U.S. Cl.
  CPC .............. *G21G 1/06* (2013.01); *A61N 5/1077* (2013.01); *A61N 2005/109* (2013.01); *A61N 2005/1087* (2013.01); *G21G 2001/0089* (2013.01)

(58) Field of Classification Search
  CPC .......... A61N 5/1077; A61N 2005/1087; A61N 2005/109; G21G 1/06; G21G 2001/0089
  See application file for complete search history.

(56) References Cited

U.S. PATENT DOCUMENTS

| | | | |
|---|---|---|---|
| 5,355,394 A * | 10/1994 | van Geel | A61K 51/1282 376/170 |
| 5,784,424 A | 7/1998 | Fries et al. | |
| 6,299,666 B1 | 10/2001 | Apostolidis et al. | |
| 2007/0092051 A1* | 4/2007 | Adelman | G21G 1/06 376/158 |
| 2009/0191122 A1* | 7/2009 | Moreno Bermudez | G21G 4/08 424/1.61 |
| 2011/0200154 A1* | 8/2011 | Nolen, Jr. | G21G 1/001 376/194 |
| 2016/0189816 A1* | 6/2016 | Czerwinski | G21C 19/42 376/189 |
| 2020/0082956 A1* | 3/2020 | Brown | G21G 1/12 |

OTHER PUBLICATIONS

Anderson et al., "Design, Construction, and Modeling of a 252Cf Neutron Irradiator", Science and Technology of Nuclear Installations, vol. 2016, Article ID 9012747.
Morgenstern et al., "Supply and Clinical Application of Actinium-225 and Bismuth-213", Seminars in Nuclear Medicine, 119-123, 2020.
Spicer et al., "Protons Ejected from Nickel by 17.5 MeV Bremsstrahlung", CSIRO Australia, 1956.

* cited by examiner

Primary Examiner — Thaddeus B Cox
(74) Attorney, Agent, or Firm — W&C IP (57) ABSTRACT

An Actinium-225 generator is provided. The generator includes a neutron source; a neutron target arranged to receive neutrons emitted from the neutron source, wherein the neutron target comprises nickel; and a proton target arranged to receive protons emitted from the neutron target, wherein the proton target comprises radium-226. Methods for producing Actinium-225 are also provided.

15 Claims, 10 Drawing Sheets

SYSTEMS AND METHODS FOR PRODUCING ACTINIUM-225

FIELD OF THE INVENTION

The invention is generally related to an Actinium-225 generator in which neutrons are incident on a first material to generate high energy protons, and the generated protons are then incident on a second material comprising radium-226 to produce Actinium-225.

BACKGROUND OF THE INVENTION

Recent studies have shown that mortality in men due to prostate cancer is above 358,000 worldwide, and is ranked as the second most frequent cancer after lung cancer [1]-[3]. Metastatic castration-resistant prostate cancer (mCRPC) is an advanced prostate cancer [4], [5], for which clinicians use prostate-specific membrane antigen (PSMA) as a metastatic prostate cancer indicator [6]. This advanced stage of prostate cancer can be considered as a non-curable disease depending on the PSMA level. Recent studies and clinical reports show that molecular radiotherapy using radionuclides such as Lu-177, Bi-213, and Ac-225 [7], [8] can increase the survival rate of patients [7], [9]-[12]. This involves labelling the PSMA with high Alpha or Beta emitter sources for their high Linear Energy Transfer LET and Relative Biological Effect (RBE). Acitnium-225 is the preferred radionuclide as it is an alpha emitter and has both high LET and RBE almost 100 times more than Beta emitters [6].

The generated amount of these radiopharmaceuticals is a major challenge as the demand is high while the supply is not sufficient [12]. Several studies were reported by Morgenstern et al. for producing Ac-225, most of which are still under research. Methods that have been proposed to produce Ac-225 only serve as a ready to use Ac-225 in a vial or an Ac-225/Bi-213 generator [10], [13], [14]. A major limitation for generating Ac-225 is its short half-life of around 10 days [15]. As a result, transporting this radionuclide to serve patient needs is difficult worldwide and specifically in low and middle income countries.

Thus, new systems and methods for producing Actinium-225 are needed.

SUMMARY

The present disclosure provides a device and method for producing Actinium-225 using a two-stage process: neutrons incident on a first material to generate high energy protons, and the generated protons are then incident on a second material (radium-226) to produce Actinium-225.

An aspect of the disclosure provides an Actinium-225 generator, comprising a neutron source; a neutron target arranged to receive neutrons emitted from the neutron source, wherein the neutron target comprises nickel, manganese, or iron; and a proton target arranged to receive protons emitted from the neutron target, wherein the proton target comprises radium-226. In some embodiments, the neutron target and the proton target are concentric cylinders surrounding the neutron source.

In some embodiments, the neutron source has a source activity of at least 1E15 Bq. In some embodiments, the neutron source has a source activity of at least 14 MeV. In some embodiments, the neutron source is Californium-252. In some embodiments, the neutron target comprises nickel and has a thickness of 0.01-0.06 mm. In some embodiments, the proton target comprises $RaCl_2$ and has a thickness of 4.5-5.5 mm.

Another aspect of the disclosure provides a method of producing Actinium-225, comprising bombarding a neutron target with neutrons from a neutron source to produce a proton beam, wherein the neutron target comprises nickel, manganese, or iron; and bombarding a proton target with the proton beam, wherein the proton target comprises radium-226. In some embodiments, a proton energy of the proton beam is 10 MeV or higher.

DETAILED DESCRIPTION

Embodiments of the disclosure provide an Actinium-225 generator, comprising a neutron source; a neutron target arranged to receive neutrons emitted from the neutron source, wherein the neutron target comprises nickel, manganese, or iron; and a proton target arranged to receive protons emitted from the neutron target, wherein the proton target comprises radium-226.

Figure 10:
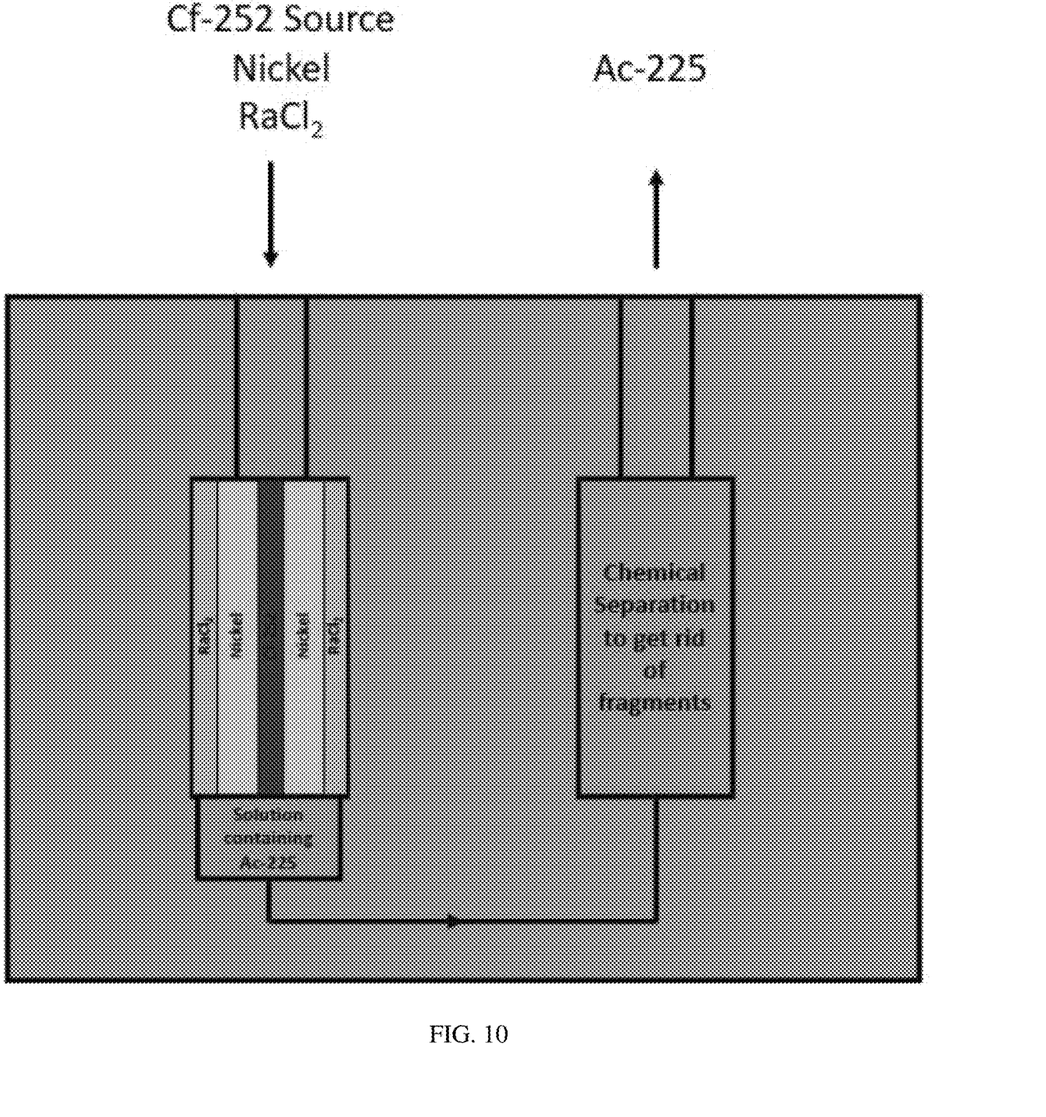
FIG. 10. Actinium-225 generator according to some embodiments of the disclosure.

As shown in FIG. 10, in some embodiments, the neutron target and the proton target are concentric cylinders surrounding the neutron source. In particular, the generator may comprise three concentric cylinders. The innermost is made from a neutron source such as Californium-252 (Cf-252), the middle cylinder is made from nickel, manganese, or iron, and the outer cylinder is made from radium-226 (e.g. $RaCl_2$). The cylinders may be formed from a thin sheet or foil. In some embodiments, the cylinder comprises a volume in which a solution containing the target material (e.g. radium) is disposed.

A neutron source is any device that emits neutrons, irrespective of the mechanism used to produce the neutrons. In some embodiments, the neutron source has a source activity of at least 1E15 Bq, for example, at least 7.15E12 Bq. In some embodiments, the neutron source has a source activity of at least 14 MeV.

Certain isotopes undergo spontaneous fission with emission of neutrons. The most commonly used spontaneous fission source is the radioactive isotope californium-252. $^{252}Cf$ and all other spontaneous fission neutron sources are produced by irradiating uranium or another transuranic element in a nuclear reactor, where neutrons are absorbed in the starting material and its subsequent reaction products, transmuting the starting material into the SF isotope. $^{252}$Cf neutron sources are typically ¼" to ½" in diameter and 1" to 2" in length. A typical $^{252}$Cf neutron source emits between $1\times10^7$ to $1\times10^9$ neutrons per second and has a half-life of 2.6 years.

In some embodiments, any known neutron generator such as a sealed tube neutron generator is used as the neutron source. Suitable neutron generators include a lightweight portable neutron generator, such as the Thermo Scientific MP320 generator or other generators that can produce high energy neutrons. If a neutron generator is used, the neutron target and and proton target may be provided as slabs placed next to the generator instead of two concentric cylinders. The neutron beam travels some distance before leaving the generator. The two slabs can be placed next to the neutron generator window or with a custom made neutron generator can be placed directly after the neutron beam. In any embodiment, a proton-impervious beam stop may be placed downstream of the targets.

The neutron target comprises metal atoms on which the high-energy neutrons impinge. If the incident neutrons strike a metal atom with numerous nucleons, the result is spallation, meaning evaporation of protons and neutrons. An intranuclear cascade is created in the nucleus of the metal atom in which protons are emitted. The neutrons impinging on the metal atoms cause the nuclei of the metal atoms to break up, there is a fragmentation of the metal atom into several nuclei and then vaporization of charged particles. The protons generated by cascade processes have higher energy, corresponding to the higher energy of the impinging neutrons.

Actinium-225 production is dependent on the proton flux and energy. In some embodiments, the neutron target comprises nickel and has a thickness of 0.01-1 mm, e.g. 0.01-0.06 mm or about 0.5 mm. In some embodiments, the neutron target comprises iron or manfanese and has a thickness of 0.01-1 mm, e.g. 0.2-0.3 mm or about 0.25 mm Other suitable neutron targets include, but are not limited to, aluminum, silicon, potassium, copper, zinc, germanium, and various types of steel such as stainless steel.

In some embodiments, the proton target comprises radium chloride ($RaCl_2$) and has a thickness of 4.5-5.5 mm, e g about 5 mm $RaCl_2$ may be obtained from precipitation with concentrated HCl, or radium carbonate $RaCO_3$.

In some embodiments, a chemical separation stage is connected to the generator to remove unwanted isotopes or fragments generated by the irradiation process. Some of the isotopes may be radioactive and thus the chemical separation stage allows for the production of a pure Actinium-225 solution that does not contain other radioactive materials to ensure the dose delivered to the patient is optimized. One example of chemical separation is described in Apostolidis et al. Anal. Chem. 77 (2005) 6288. Commercial products such as the DOWEX resins from Dow Chemical are specifically designed to separate actinium in aqueous solution and may be utilized in a process as disclosed herein.

Additional shielding, such as a lead, concrete, or water barrier, may be placed around the generator to protect the users from neutrons and gamma rays.

Embodiments of the disclosure also provide a method of producing Actinium-225, comprising bombarding a neutron target with neutrons from a neutron source to produce a proton beam, wherein the neutron target comprises nickel, manganese, or iron; and bombarding a proton target with the proton beam, wherein the proton target comprises radium-226. Neutrons produced by a radioactive isotope or a neutron generator will hit the neutron target which is a metal such as nickel, manganese, or iron. The metal target generates high energy protons. The protons hit a target that contains radium (Ra) in any physical form. Actinium 225 is produced along with several other isotopes that can be filtered out by a chemical extraction stage to provide purified Ac-225. In some embodiments, a proton energy of the proton beam is 10 MeV or higher, e.g at least 11, 12, 13, 14, or 15 MeV.

Before exemplary embodiments of the present invention are described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

The invention is further described by the following non-limiting examples which further illustrate the invention, and are not intended, nor should they be interpreted to, limit the scope of the invention.

EXAMPLE

Summary

Actinium-225 is used in nuclear medicine for treatment of malignant tumors. It can be applied to produce Bi-213 in a reusable generator or can be used alone as an agent for radiation therapy, in, particular for targeted alpha therapy. However, the availability of Actinium-225 for worldwide use, particularly in low and middle income countries, is limited. We present a feasibility study employing GATE, an open source Monte Carlo simulation toolkit, on the production of Actinium-225 from a neutron generator. This work shows that a design comprising three concentric cylinders, the innermost a Cf-252 neutron source, the middle nickel cylinder acting as a neutron target and the outer cylinder a RaCl2 proton target provides a feasible design for an Actinium-225 generator.

Materials and Methods

Figure 1:
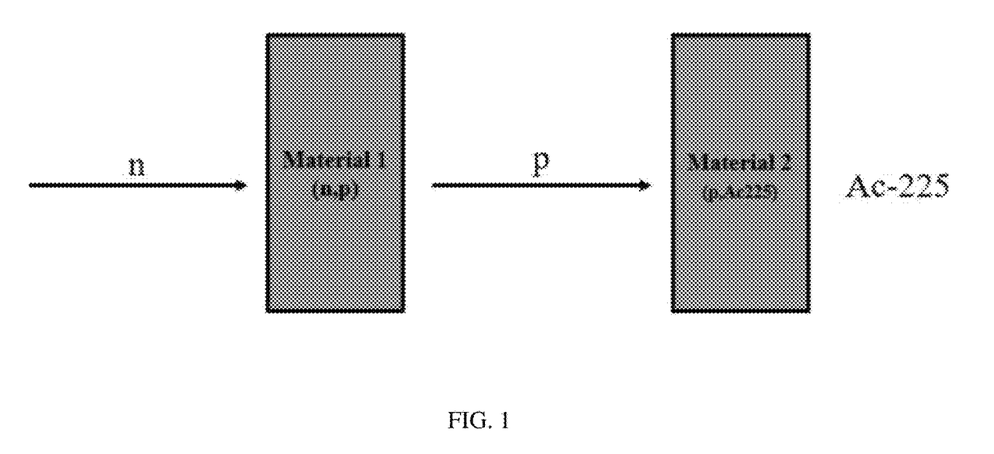
FIG. 1. Actinium-225 generation process according to some embodiments of the disclosure.

Several research studies have been published explaining the different methods of generating Ac-225 [10], [13], [14]. The accelerator method that uses Ra-226 has been investigated theoretically and experimentally and shows promising results [12], [16], [17]. The target of $RaCl_2$ can be irradiated by proton particles, neutrons or gamma rays [16]. In this work, we evaluated generating Ac-225 in a two-stage process: neutrons incident on material 1 (FIG. 1) to generate high energy protons, and the generated protons will then be incident on material 2, which is the $RaCl_2$ in this study. The evaluation was carried out using GATE Monte-Carlo simulation toolkit.

GATE is an open-source Monte Carlo simulation toolkit. It incorporates the well-validated physics of GEANT4 with a more user-friendly simulation environment [18]. GATE has shown great potential in a wide range of medical applications, including radiotherapy [19]-[21], diagnostic radiology [22], [23], and dosimetry [24]-[26].

Figure 2:
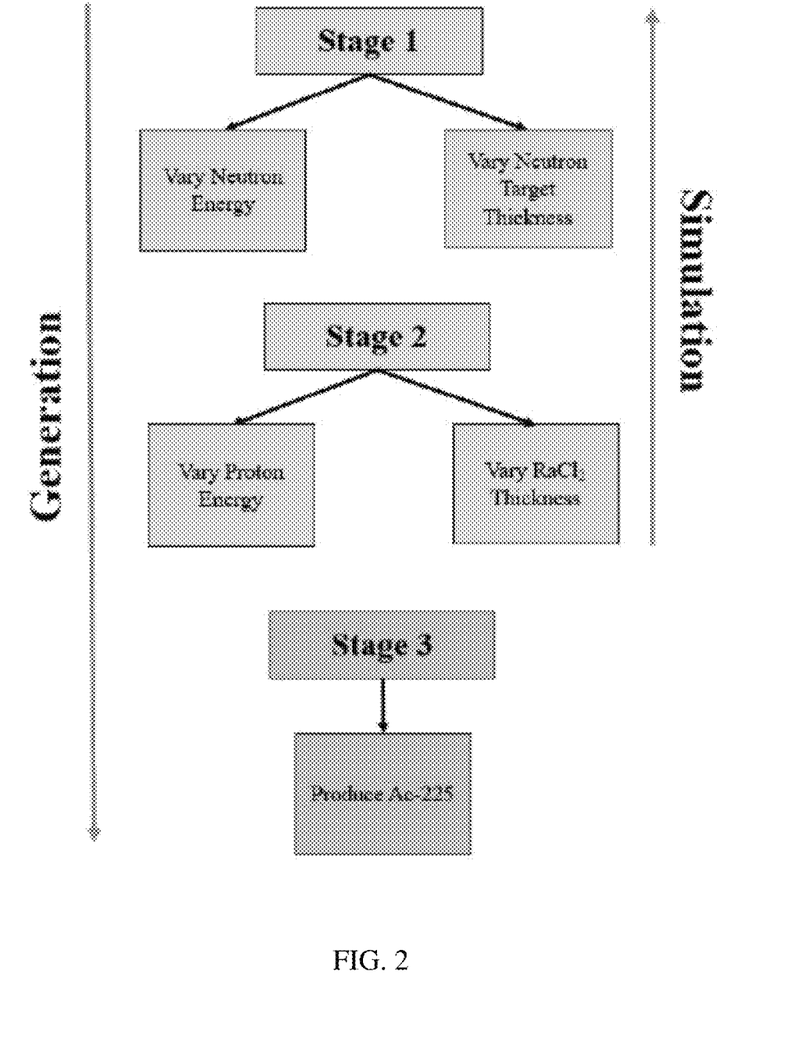
FIG. 2. Flow-chart showing the two stages employed to determine the optimum parameters for Actinium-225 generation.

The simulation can be split into 3 stages. The first two stages focus on finding the optimum parameters for producing Ac-225 using a $RaCL_2$ target (see FIG. 2), while the third employs these parameters into studying the feasibility and viability of producing the radionuclide using said stages. The quark gluon string model with high neutron precision package 'QGSP_BIC_HP' was used. This reference physics package provides a good description of secondary particles produced by protons and neutrons in addition to a very reliable transport modeling for neutrons below 20 MeV [27].

The First Simulation Stage

The first simulation stage involves finding the proton energy threshold for producing Ac-225 by bombarding an $RaCl_2$ target with high energy protons. This is achieved by embedding a monoenergetic proton point source at the center of a proton target composed of a Radium Chloride (RaCl2) cylinder. Both the proton energy and the proton target thicknesses are varied to find the optimum conditions for producing Ac-225. Proton energies considered in this set of experiments are 2, 5, 7.5, 10, 15, and 20 MeV. Thicknesses considered are 0.04, 0.06, 0.08, 0.1, 0.25, and 1 mm. The number of particles used in this stage was 108.

The Second Simulation Stage

In the second simulation stage, the objective was to find the neutron energy and target material required to produce protons that meet the minimum requirements found in the previous step for producing Ac-225. Therefore, a neutron monoenergetic point source is placed at the center of a cylindrical neutron target. The neutron energy, cylinder material and its thickness are varied. For each run, the energy spectrum of the produced protons is recorded. The feasibility of each neutron energy, material type and thickness depend on the produced protons quantity and energy. Several materials were investigated, including Nickel (Ni), Iron (Fe), Potassium (K), Stainless-Steel (SS), Magnesium (Mg), and Manganese (Mn). The number of particles used in this stage was 108.

The Final Production Stage

The outcomes of the first and second stages form the basis of the third stage. The setup of the third stage comprises two cylinders: an inner and an outer cylinder. The inner cylinder acts as the neutron target. The neutron target composition and thickness are dependent on the outcomes of the second stage. The outer cylinder represents the proton target and is composed of $RaCl_2$ with the optimum thickness found in the first stage. At the center of the neutron target, a point neutron source is placed. All available neutron sources with energies meeting the criteria are used against this setup to find the probability of producing Ac-225 for each neutron source.

The number of protons produced by neutrons is expected to be relatively low. Therefore, to avoid high statistical uncertainty in calculating Ac-225 production probability, a very thin virtual layer (1 μm) is placed between the two cylinders. The purpose of this layer is to record the properties of all protons produced in the neutron target and leaving its volume toward the proton target. When the neutron target is bombarded with 108 neutrons, some protons will be produced. Several of these protons will leave the neutron target and transverse the thin layer where their momentum and spatial properties are stored in a phase space file. Subsequently, the simulation is relaunched using the same setup but with the neutron source being replaced by a proton source. This proton source emits from the phase-space layer with the source properties derived from the phase space file. The number of protons emitted from the phase-space file is set to 5×106 and by that, the number of protons is amplified by a factor ranging approximately from 104 to 105.

Results and Discussion

Figure 3:
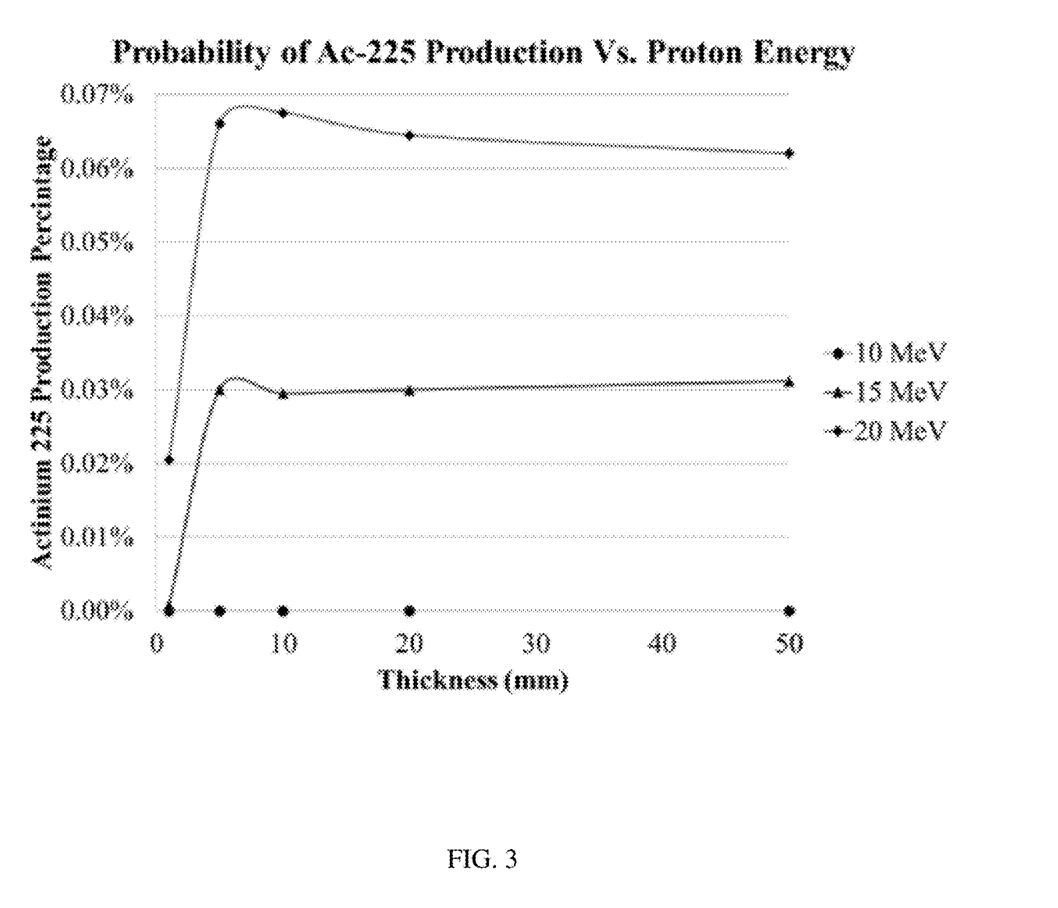
FIG. 3. Probability of producing Actinium-225 as a function of proton energy.

The process for producing Actinium-225 from $RaCl_2$ material depends mainly on the proton energy interacting with $RaCl_2$. FIG. 3 shows the dependence of producing Ac-225 on the proton energy. Even though 6 proton energies were simulated in the first stage, starting at 2.5 MeV, the figure only shows three curves because the probability of producing Ac-225 from protons with energies below or equal to 10 MeV is between 0.0006% and 0.0008%. The best $RaCl_2$ thickness to produce Ac-225 for 15 MeV and 20 MeV protons was determined to be 5 mm. To calculate the activity of the generated Actinium using the curves from FIG. 3, a 1 Ci proton source incident on a 5 mm thick $RaCl_2$ target will result in 32 uCi and 68 uCi for the 10 MeV and the 15 MeV proton energies respectively.

Figure 4:
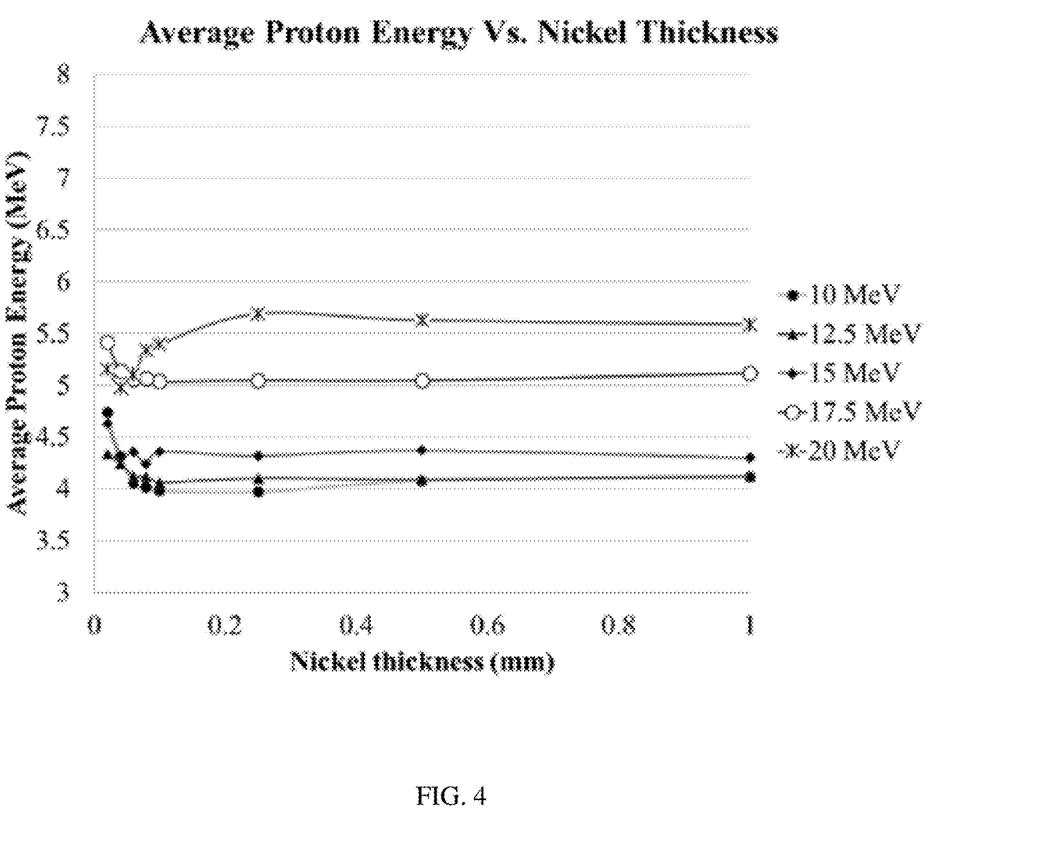
FIG. 4. Average proton energy generated from neutron beams interacting with nickel at several thicknesses.

The generation of high energy protons is key to producing Actinium as shown in FIG. 3. To produce high energy protons inside the Ac-225 generator, a neutron beam with energies from 10 MeV up to 20 MeV were incident on Nickel (Ni), Iron (Fe), Potassium (K), Stainless-Steel (SS), Magnesium (Mg), and Manganese (Mn). The following discussion is for Nickel, Manganese, and Iron as they produced the best results. FIG. 4 shows the proton average energy generated at different nickel thicknesses from a neutron beam with 10, 12.5, 15, 17.5, and 20 MeV. It should be noted that the maximum proton energy generated cannot exceed the maximum neutron energy from the (n,p) reaction. The figure demonstrates that the higher the neutron energy, the higher the average proton energy generated at all suggested nickel thickness. The maximum thickness in the x-axis for FIG. 4 is 1 mm because thicker materials would absorb the proton since charged particles start to interact as soon as they are generated.

The average produced protons energy ranges from 0 to approximately the maximum incident neutron energy, i.e. a 10 MeV neutron can produce 10 MeV protons, because of the conservation of energy. The incident neutron energy and the average produced proton energy are directly proportional. The maximum average proton energy was around 5.6 MeV at 0.25 mm from the 20 MeV neutrons.

Figure 5:
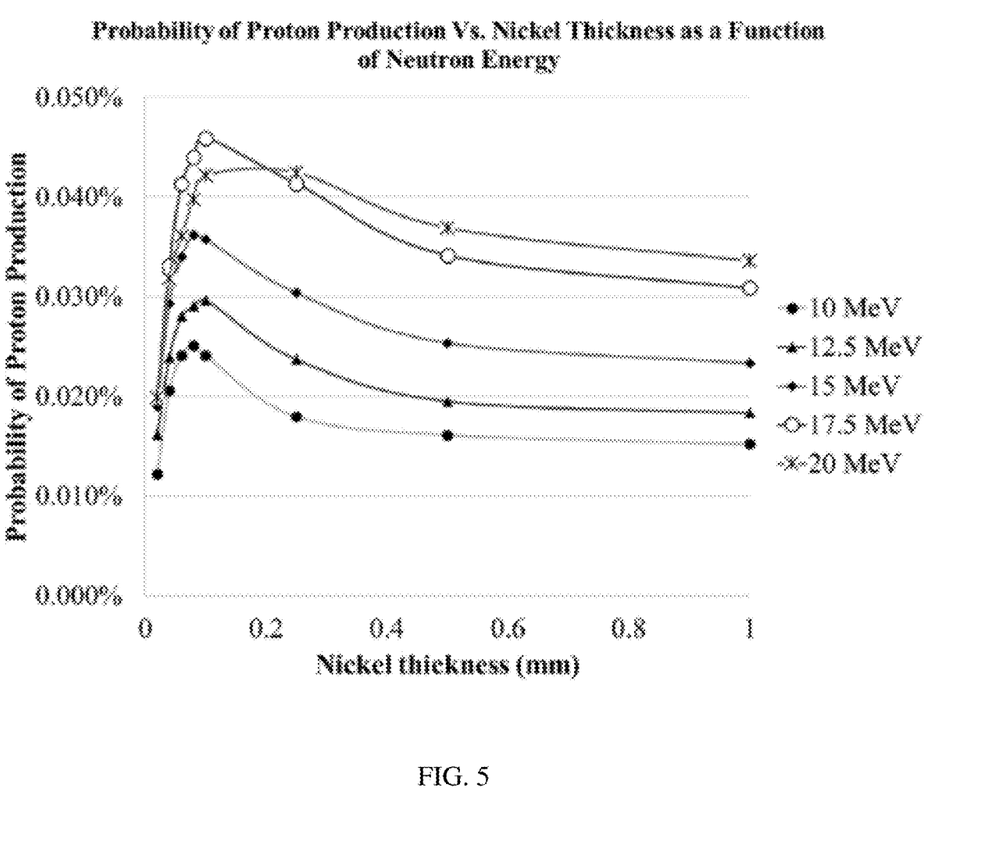
FIG. 5. Probability of proton production from neutrons incident on nickel at different thicknesses.

FIG. 5 shows the probability of producing protons at the same nickel thicknesses used in FIG. 4 as a function of neutron energy. The probability is maximum at 0.1 mm thickness for the 17.5 MeV neutron energy, and slowly decreases as the nickel thickness increases for all other neutron energies.

Figure 6:
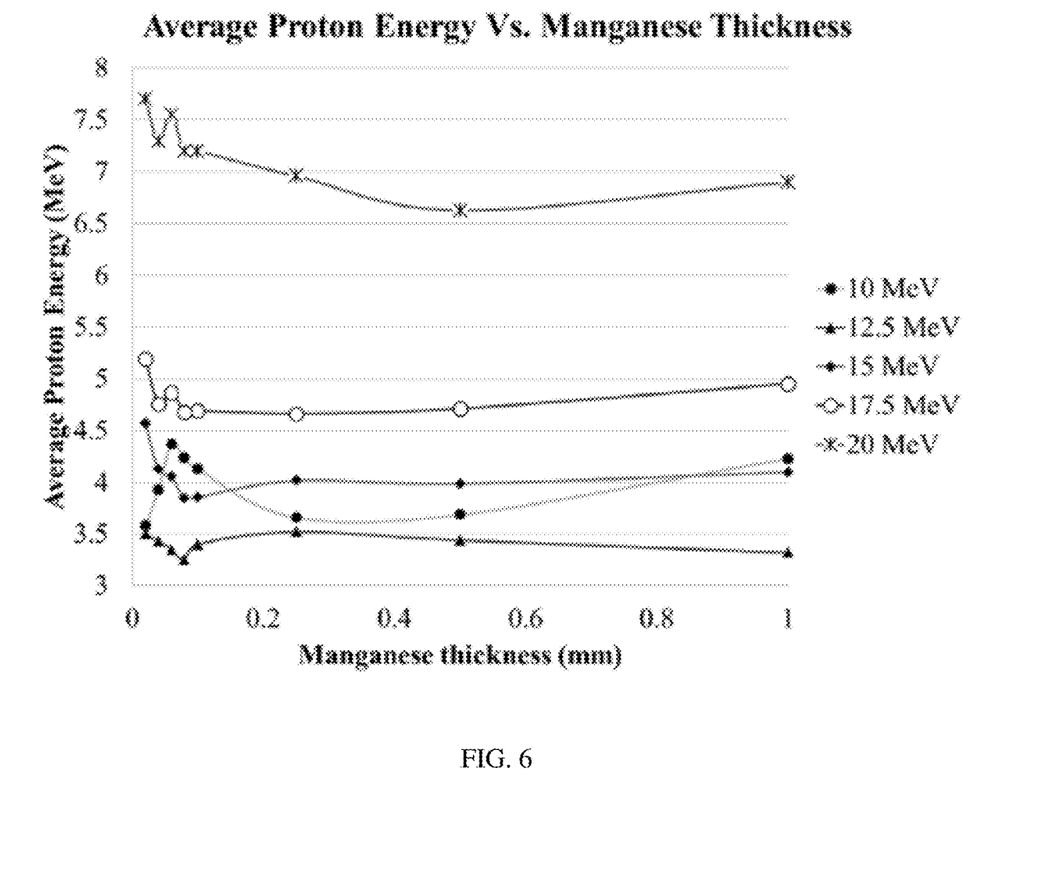
FIG. 6. Average proton energy generated from neutron beams interacting with manganese at several thicknesses.

FIG. 6 shows the average proton energy generated at different manganese thicknesses from a neutron beam with 10, 12.5, 15, 17.5, and 20 MeV. The figure confirms what was demonstrated in the nickel case, where the higher the neutron energy, the higher the average proton energy generated is at all thicknesses. The maximum thickness was kept to 1 mm to reduce the probability of proton absorption in the manganese. The maximum average proton energy generated by 20 MeV neutrons is approximately 7.7 MeV at ~0.05 mm, which is higher than the nickel case.

Figure 7:
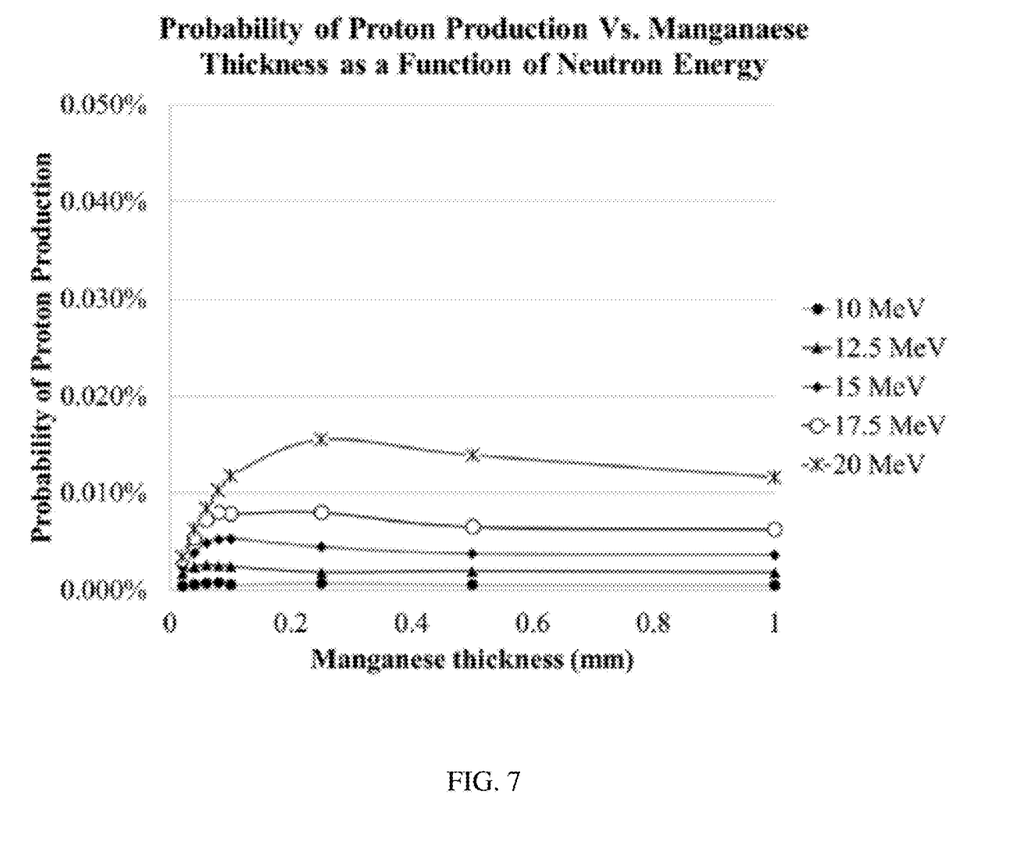
FIG. 7. Probability of proton production from neutrons incident on manganese at different thicknesses.

FIG. 7 shows the probability of producing protons at different manganese thicknesses as a function of neutron energy. The probability is maximum at 0.25 mm thickness for the 20 MeV neutron energy and decreases as the neutron energy decrease. There is a tradeoff between the maximum average proton energy that can be produced by nickel and manganese and the probability of producing the protons for the two metals.

Figure 8:
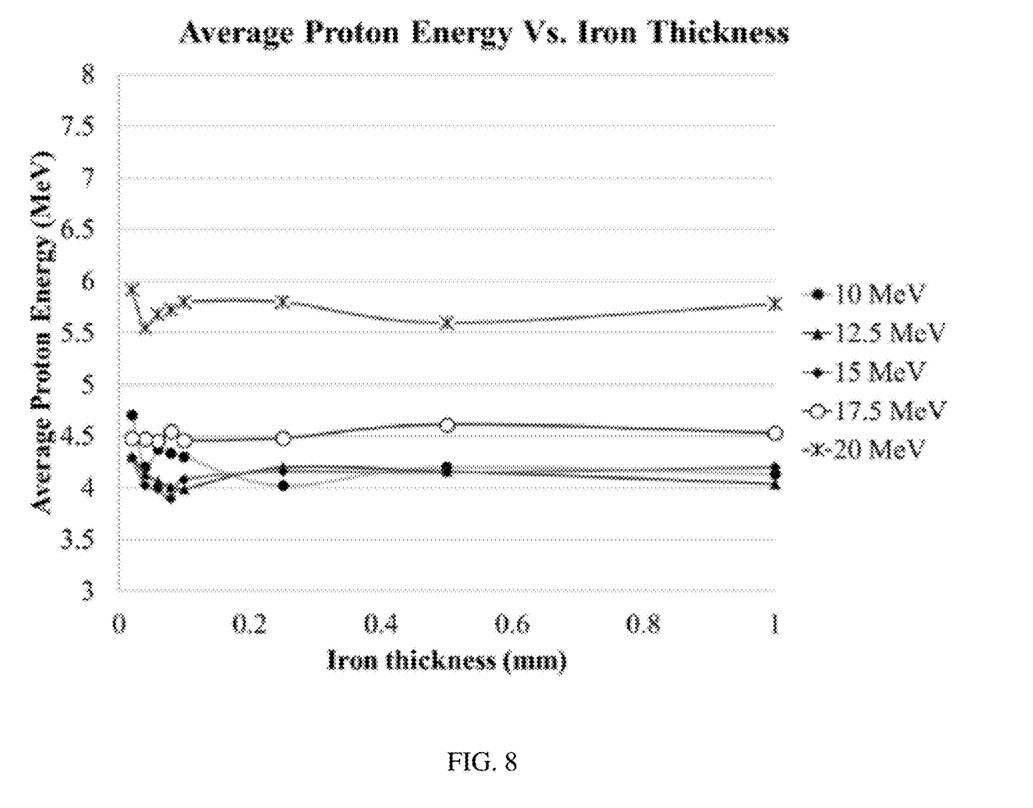
FIG. 8. Average proton energy generated from neutron beams interacting with iron at several thicknesses.

FIG. 8 shows the average proton energy generated at different iron thicknesses from a neutron beam with 10, 12.5, 15, 17.5, and 20 MeV. The figure follows the same trend observed in the nickel and manganese cases, where the higher the incident neutron energy is, the higher the average proton energy is generated at all thicknesses. The maximum average proton energy generated by 20 MeV neutrons is around 6 MeV at ~0.05 mm, which is slightly higher than the nickel case.

Figure 9:
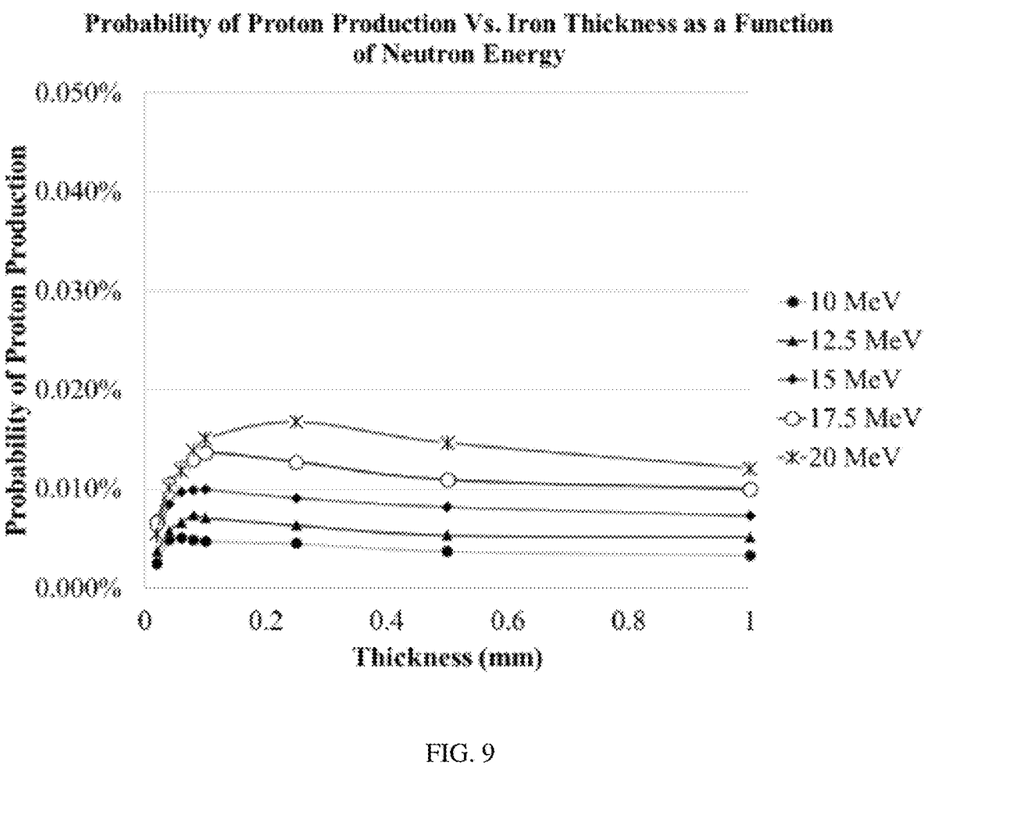
FIG. 9. Probability of proton production from neutrons incident on iron at different thicknesses.

FIG. 9 shows the probability of producing protons at different iron thicknesses as a function of neutron energy. The probability is maximum at 0.25 mm thickness for the 20 MeV neutron energy and decreases as the neutron energy decrease. The iron and manganese have similar proton production probabilities, both are equal but less than the nickel case.

Combining the results for nickel, manganese, and iron, it can be concluded that the neutron source must possess an energy greater than 10 MeV to produce Ac-225 in addition to a high probability of producing protons. Since Cf-252 emits a spectrum of energies, additional simulations were run to find the optimum nickel thickness between 0.01 and 0.06 mm. The 0.01 mm thickness produced 3.3 MeV average proton energy and the 0.05 mm thickness produced 2.7 MeV average energy with about 90% more protons than the 0.01 mm thickness. Thus, the 0.05 mm of nickel was chosen to be paired with Cf252.

On the other hand, all $RaCl_2$ thicknesses produced a similar amount of Ac-225, and so a 1 cm thickness was used. The simulation results showed that in order to produce a single Ac-225 atom, a Cf-252 source with an estimated activity of 7.15E12 Bq is needed. A further set of simulations was run replacing the Cf-252 with a typical neutron generator with a 14 MeV energy. The activity needed to produce a single Ac-225 atom with the neutron generator is 2.21E9 Bq. The Cf-252 and the neutron generator both produced isotopes/fragments in addition to the Ac-225. Some of the isotopes are radioactive and some are not, so the chemical separation stage is important to produce pure an Ac-225 solution that does not contain other radioactive materials to ensure the dose delivered to the patient is optimized.

CONCLUSION

It has been demonstrated by employing GATE, an open source Monte Carlo simulation toolkit, that the production of Actinium-225 from a neutron generator is feasible. This work shows that a design comprising three concentric cylinders, the innermost a Cf-252 neutron source, the middle nickel cylinder acting as a neutron target and the outer cylinder a $RaCl_2$ proton target provides a feasible design for an Actinium-225 generator. The optimum dimensions for the neutron target are 0.05 mm nickel and the optimum $RaCl_2$ thickness to produce Ac-225 was determined to be 5 mm Such a design will help address the issue of a lack of radiopharmaceutical production to address worldwide demand, particularly in low and middle income countries.

ACKNOWLEDGMENTS

This project was funded by the Deanship of Scientific Research (DSR) at King Abdulaziz University, Jeddah, under grant no. (RG-28-135-38). The inventors, therefore, gratefully acknowledge DSR technical and financial support.

REFERENCES

[1] A. Villers and P. Grosclaude, "Epidemiologic du cancer de la prostate," *Médecine Nucléaire*, vol. 32, no. 1, pp. 2-4, January 2008, doi: 10.1016/j.mednuc.2007.11.003.

[2] G. The Global Cancer Observatory, "Prostate 2018," *World Heal. Organ.*, vol. 876, p. 1, 2, 2019.

[3] F. Bray, J. Ferlay, I. Soerjomataram, R. L. Siegel, L. A. Torre, and A. Jemal, "Global cancer statistics 2018: GLOBOCAN estimates of incidence and mortality worldwide for 36 cancers in 185 countries," *CA. Cancer J. Clin.*, vol. 68, no. 6, pp. 394-424, 2018, doi: 10.3322/caac.21492.

[4] B. J. Davison, M. E. Gleave, S. L. Goldenberg, L. F. Degner, D. Hoffart, and J. Berkowitz, "Assessing information and decision preferences of men with prostate cancer and their partners," *Cancer Nurs.*, vol. 25, no. 1, pp. 42-49, January 2002.

[5] M. S. Hofman et al., "[177 Lu]-PSMA-617 radionuclide treatment in patients with metastatic castration-resistant prostate cancer (LuPSMA trial): a single-centre, single-arm, phase 2 study," *Lancet Oncol.*, vol. 19, no. 6, pp. 825-833, June 2018, doi: 10.1016/S1470-2045(18)30198-0.

[6] Y. Li, Z. Tian, S. Rizvi, N. Bander, B. Allen, and S. Wales, "In vitro and preclinical targeted alpha therapy of human prostate cancer with Bi-213 labeled J591 antibody against the prostate specific membrane antigen," *Prostate Cancer Prostatic Dis.*, vol. 5, pp. 36-46, 2002, doi: 10.1038/sj/pcan/4500543.

[7] E. Azorín-Vega, E. Rojas-Calderon, G. Ferro-Flores, L. Aranda-Lara, N. Jimenez-Mancilla, and M. A. Nava-Cabrera, "Assessment of the radiation absorbed dose produced by 177 LuiPSMA, 225 Ac-iPSMA and 223 RaCl 2 to prostate cancer cell nuclei in a bone microenvironment model," *Appl. Radiat. Isot.*, vol. 146, no. January, pp. 66-71, 2019, doi: 10.1016/j.apradiso.2019.01.020.

[8] J. Ahn, S. Park, B. Zuniga, A. Bera, C. S. Song, and B. Chatterjee, "Vitamin D in Prostate Cancer," in *Vitamins and Hormones*, vol. 100, Academic Press Inc., 2016, pp. 321-355.

[9] D. L. Ludwig et al., "Preclinical Development of an Actinium-225-Labeled Antibody Radio-Conjugate Directed Against CD45 for Targeted Conditioning and Radioimmunotherapy," *Biol. Blood Marrow Transplant.*, vol. 26, no. 3, pp. S160-S161, 2020, doi: 10.1016/j.bbmt.2019.12.714.

[10] M. Miederer, D. A. Scheinberg, and M. R. McDevitt, "Realizing the potential of the Actinium-225 radionuclide generator in targeted alpha particle therapy applications," *Adv. Drug Deliv. Rev.*, vol. 60, no. 12, pp. 1371-1382, 2008.

[11] Y. Dekempeneer et al., "Targeted alpha therapy using short-lived alpha-particles and the promise of nanobodies as targeting vehicle," *Expert Opin. Biol. Ther.*, vol. 16, no. 8, pp. 1035-1047, 2016, doi: 10.1080/14712598.2016.1185412.

[12] A. Morgenstern, C. Apostolidis, and F. Bruchertseifer, "Supply and Clinical Application of Actinium-225 and Bismuth-213," *Semin. Nucl. Med.*, vol. 50, no. 2, pp. 119-123, 2020, doi: 10.1053/j.semnuclmed.2020.02.003.

[13] O. Artun, "Estimation of the production of medical Ac-225 on thorium material via proton accelerator," *Appl. Radiat. Isot.*, vol. 127, pp. 166-172, 2017, doi: 10.1016/j.apradiso.2017.06.006.

[14] K. Kossert, M. P. Takács, and O. Nähle, "Determination of the activity of 225Ac and of the half-lives of 213Po and 225Ac," *Appl. Radiat. Isot.*, vol. 156, no. November 2019, 2020, doi: 10.1016/j.apradiso.2019.109020.

[15] F. H. Ruddy, A. R. Dulloo, J. G. Seidel, and B. Petrović, "Separation of the alpha-emitting radioisotopes actinium-225 and bismuth-213 from thorium-229 using alpha recoil methods," *Nucl. Instruments Methods Phys. Res. Sect. B Beam Interact. with Mater. Atoms*, vol. 213, pp. 351-356, 2004, doi: 10.1016/50168-583X(03)01580-5.

[16] C. Apostolidis, R. Molinet, J. McGinley, K. Abbas, J. Möllenbeck, and A. Morgenstern, "Cyclotron production of Ac-225 for targeted alpha therapy," *Appl. Radiat. Isot.*, vol. 62, no. 3, pp. 383-387, 2005, doi: 10.1016/j.apradiso.2004.06.013.

[17] F. Bruchertseifer, A. Kellerbauer, R. Malmbeck, and A. Morgenstern, "Targeted alpha therapy with bismuth-213 and actinium-225: Meeting future demand," *Journal of Labelled Compounds and Radiopharmaceuticals*, vol. 62, no. 11. pp. 794-802, 2019, doi: 10.1002/jlcr.3792.

[18] S. Jan et al., "GATE: a simulation toolkit for PET and SPECT," *Phys. Med. Biol.*, vol. 49, no. 19, pp. 4543-4561, 2004, doi: 10.1088/0031-9155/49/19/007.

[19] L. Grevillot, D. Bertrand, F. Dessy, N. Freud, and D. Sarrut, "A Monte Carlo pencil beam scanning model for proton treatment plan simulation using GATE/GEANT4," *Phys. Med. Biol.*, vol. 56, no. 16, pp. 5203-5219, August 2011, doi: 10.1088/0031-9155/56/16/008.

[20] L. Grevillot et al., "Technical Note: GATE-RTion: a GATE/Geant4 release for clinical applications in scanned ion beam therapy," *Med. Phys.*, p. mp.14242, June 2020, doi: 10.1002/mp.14242.

[21] Z. Aitelcadi, Y. Toufique, A. El Kharrim, S. Elmadani, A. Hilali, and O. Bouhali, "Validation of the GATE Monte Carlo code for radiation therapy: Varian Clinac2300C/D," in 2018 *4th International Conference on Optimization and Applications (ICOA)*, April 2018, pp. 1-4, doi: 10.1109/ICOA.2018.8370602.

[22] P. Aguiar, E. Casarejos, J. Silva-Rodriguez, J. A. Vilan, and A. Iglesias, "Geant4-GATE Simulation of a Large Plastic Scintillator for Muon Radiography," *IEEE Trans. Nucl. Sci.*, vol. 62, no. 3, pp. 1233-1238, June 2015, doi: 10.1109/TNS.2015.2431297.

[23] F. Lamare, A. Turzo, Y. Bizais, C. C. Le Rest, and D. Visvikis, "Validation of a Monte Carlo simulation of the Philips Allegro/GEMINI PET systems using GATE," *Phys. Med. Biol.*, vol. 51, no. 4, pp. 943-962, February 2006, doi: 10.1088/0031-9155/51/4/013.

[24] P. Papadimitroulas, "Dosimetry applications in GATE Monte Carlo toolkit," *Phys. Medica*, vol. 41, pp. 136-140, September 2017, doi: 10.1016/j.ejmp.2017.02.005.

[25] C. O. Thiam, V. Breton, D. Donnarieix, B. Habib, and L. Maigne, "Validation of a dose deposited by low-energy photons using GATE/GEANT4," *Phys. Med. Biol.*, vol. 53, no. 11, pp. 3039-3055, June 2008, doi: 10.1088/0031-9155/53/11/019.

[26] D. Villoing, S. Marcatili, M.-P. Garcia, and M. Bardies, "Internal dosimetry with the Monte Carlo code GATE: validation using the ICRP/ICRU female reference computational model," *Phys. Med. Biol.*, vol. 62, no. 5, pp. 1885-1904, March 2017, doi: 10.1088/1361-6560/62/5/1885.

[27] Geant4 Collaboration, "Physics Reference Manual," 2018.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. An Actinium-225 generator, comprising:
   a neutron source;
   a neutron target arranged to receive neutrons emitted from the neutron source, wherein the neutron target comprises nickel, manganese, or iron; and
   a proton target arranged to receive protons emitted from the neutron target, wherein the proton target comprises radium-226.

2. The Actinium-225 generator of claim 1, wherein the neutron target and the proton target are concentric cylinders surrounding the neutron source.

3. The Actinium-225 generator of claim 1, wherein the neutron source has a source activity of at least 1E15 Bq.

4. The Actinium-225 generator of claim 1, wherein the neutron source has a source activity of at least 14 MeV.

5. The Actinium-225 generator of claim 1, wherein the neutron source is Californium-252.

6. The Actinium-225 generator of claim 1, wherein the neutron target comprises nickel and has a thickness of 0.01-0.06 mm.

7. The Actinium-225 generator of claim 1, wherein the proton target comprises $RaCl_2$ and has a thickness of 4.5-5.5 mm.

8. A method of producing Actinium-225, comprising:
bombarding a neutron target with neutrons from a neutron source to produce a proton beam, wherein the neutron target comprises nickel, manganese, or iron; and
bombarding a proton target with the proton beam, wherein the proton target comprises radium-226.

9. The method of claim 8, wherein the neutron target and the proton target are concentric cylinders surrounding the neutron source.

10. The method of claim 8, wherein a proton energy of the proton beam is 10 MeV or higher.

11. The method of claim 8, wherein the neutron source has a source activity of at least 1E15 Bq.

12. The method of claim 8, wherein the neutron source has a source activity of at least 14 MeV.

13. The method of claim 8, wherein the neutron source is Californium-252.

14. The method of claim 8, wherein the neutron target comprises nickel and has a thickness of 0.01-0.06 mm.

15. The method of claim 8, wherein the proton target comprises $RaCl_2$ and has a thickness of 4.5-5.5 mm.

\* \* \* \* \*